(12) United States Patent
Feliz

(10) Patent No.: US 10,357,433 B1
(45) Date of Patent: Jul. 23, 2019

(54) SECURITY BAND FOR SECURING AND DETECTING ACCESS TO A CONTAINER

(71) Applicant: Ariel Alexander Feliz, Hollis, NY (US)

(72) Inventor: Ariel Alexander Feliz, Hollis, NY (US)

( * ) Notice: Subject to any disclaimer, the term of this patent is extended or adjusted under 35 U.S.C. 154(b) by 0 days.

(21) Appl. No.: 15/890,828

(22) Filed: Feb. 7, 2018

(51) Int. Cl.
*A61J 7/04* (2006.01)
*G08B 3/10* (2006.01)
*G04B 47/06* (2006.01)
*G16H 20/10* (2018.01)

(52) U.S. Cl.
CPC .......... *A61J 7/0436* (2015.05); *G04B 47/066* (2013.01); *G08B 3/1016* (2013.01); *G16H 20/10* (2018.01); *A61J 2200/30* (2013.01)

(58) Field of Classification Search
CPC .... B65D 47/0809; G06F 19/00; A61B 5/0004
USPC ...................................................... 340/545.6
See application file for complete search history.

(56) References Cited

U.S. PATENT DOCUMENTS

| 4,419,016 A | 12/1983 | Zoltan |
| 6,271,753 B1 | 8/2001 | Shukla |
| 6,343,695 B1 | 2/2002 | Petrick et al. |
| 7,424,888 B2 | 9/2008 | Harvey et al. |
| 8,067,935 B2 | 11/2011 | Burrows |
| 8,365,979 B2 | 2/2013 | Messmer et al. |
| 2003/0089733 A1 | 5/2003 | Cain et al. |
| 2008/0011703 A1* | 1/2008 | Schmeisser ............. B29C 45/16 215/230 |
| 2008/0169261 A1* | 7/2008 | Druitt ................ B65D 47/0809 215/237 |
| 2015/0100335 A1* | 4/2015 | Englehard ........... G06F 19/3462 705/2 |
| 2016/0034669 A1 | 2/2016 | Mahbubian |

* cited by examiner

*Primary Examiner* — Fabricio R Murillo Garcia
(74) *Attorney, Agent, or Firm* — Goldstein Law Offices, P.C.

(57) ABSTRACT

A security band for securing a container containing medication, comprising a hub and a strap, the security band is adapted to secure the container by attaching to the container in a securing position where the hub contacts the lid and the strap wraps around the bottom of the container, preventing access to medication contained within the container unless the security band is released or disturbed. The security band further comprises at least one sensor, which may be pressure switch, a first stretch sensor, or a second stretch sensor, and further comprises a control module. The pressure switch and the first and second stretch sensors detect the occurrence of an access event when the security band is released from the container or disturbed from the securing position. The control module wireless transmits an access alert signal to a user client upon the occurrence of the access event.

18 Claims, 11 Drawing Sheets

SECURITY BAND FOR SECURING AND DETECTING ACCESS TO A CONTAINER

TECHNICAL FIELD

The present disclosure relates generally to an electronic security band which restricts access to a lid on a container and detects and warns of intrusions. More particularly, the present disclosure relates to a security band which securely attaches to a container and prevents a lid on the container from being opened while the security band is attached, and further transmits an access alert to a user client in the event the security band is disturbed or released.

BACKGROUND

Conventional containers for storing medication typically include simple safety mechanisms which are only intended to prevent small children from opening the containers. Such safety mechanisms do nothing to prevent adults or older children from opening the containers and accessing the medication stored within. The risks and dangers posed by the improper consumption of medication are well known, and tragic outcomes can be prevented by better securing such containers against unauthorized access.

The challenge facing the adoption of secure containers for medication lies in the balance between safety, convenience, and reusability. Examples of various secured containers, lids, and other devices can be found within the prior art. Certain prior art containers are effective at thwarting unauthorized access, but are complex and inconvenient, which may discourage potential users from adopting such containers. Furthermore, a secure container has limited reusability as the container must be thoroughly cleaned before being reused in order to prevent contamination and the potential occurrence of a harmful reaction between newly stored medication and residue of the previously stored medication. Electronic containers in particular may be difficult to clean without damaging the electronic components, and are too expensive to be treated as disposable. Certain devices such as "smart" lids which detect the removal of the lid from the container, also face the problem of potential contamination unless thoroughly cleaned. Furthermore, containers which merely guard against unauthorized access do nothing to prevent accidental overdoses by the patient for whom the medication is intended, caused by the administering of extra doses at incorrect dosage times.

There exists an urgent need for a device which strikes a balance between convenience, safety, and reusability by being able to secure a container without contacting the medication stored within, while further reliably detecting attempts to remove or disturb the device and warning the intended patient or appropriate caretaker of any such attempts. Such a device is further capable of managing the timely consumption of medication by reminding the user if any doses are missed, and warning the user if the medication is accessed at an inappropriate time.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a security band which attaches to and secures a container having a bottom, an opening, and a lid. Accordingly, the present disclosure provides a security band comprising a hub and a strap, the hub further comprising a housing with a lower surface, an upper surface, a first connecting end, and a second connecting end, while the strap comprises an elastic strip having a first end and a second end attached to the housing at the first and second connecting ends respectively, and a central point disposed substantially midway between the first and second ends. The security band securely attaches to the container in a securing position whereby the lower surface of the housing contacts the lid and the strap wraps around the container such that the central point of the strap contacts the bottom of the container. The tension within the strap holds the hub of the security band in place over the lid, and prevents a person from accessing the lid without first releasing or disturbing the security band. The container may contain medication, chemicals, or other types of contents not intended to be generally accessible.

It is another aspect of an example embodiment in the present disclosure to provide a security band which is capable of detecting an attempt to gain access to the container and warn a user of such access. Accordingly, the security band comprises a control module contained within the housing of the hub, and pressure switch located on the lower surface of the housing. Applying pressure to the pressure switch causes the pressure switch to enter an engaged state, while releasing the pressure causes the pressure switch to enter a disengaged state. When the security band is attached to the container in the securing position, the lid contacts the pressure switch and causes it to enter the engaged state. When the security band is released from the container or disturbed, the housing and the pressure switch separate from the lid, causing the pressure switch to enter the disengaged state. The control module is operably connected to the pressure switch and is adapted to detect the occurrence of an access event when the pressure switch enters into the disengaged state from the engaged state. The control module is further adapted to wirelessly communicate with a user client, and transmits an access alert signal to the user client to notify the user of the access attempt. The user may be a patient for whose consumption the medication within the container is intended, a caretaker responsible for the well-being of the patient, a healthcare professional, or any person whose responsibility it is to maintain stocks of medication or other substances. The security band allows the user to better monitor the contents of the container to deter unauthorized access, or mitigate the consequences of such access by promptly alerting the user that access has occurred.

Yet another aspect of an example embodiment in the present disclosure is to provide a security band which detects stretching of the security band in an attempt to access the container. Accordingly, the security band may further comprise a first stretch sensor and a second stretch sensor. The first and second stretch sensors are adapted to detect a plurality of tension states within the strap, comprising a secured state and a stretched state. The first and second stretch sensors are further adapted to detect the occurrence of the access event when the tension state changes from the secured state to the stretched state. The control module is further adapted to transmit the access alert signal upon the detection of the change in tension state corresponding to the occurrence of the access event.

It is still yet another aspect of an example embodiment of the present disclosure to provide a security band which transmits security alerts to the user client beyond the range of short-ranged wireless communications. Accordingly, the control module of the security band may be adapted to transmit the alert access signal to a control server, accessible to the control module via a wide-area-network such as the Internet. The control server is adapted to relay the alert access signal to the user client via the wide area network.

It is a further aspect of an example embodiment of the present disclosure to provide a security band which assists the user in maintaining the proper dose schedule for the medication within the container. Accordingly, the user client may be configured with a dosage schedule containing scheduled dosage times. The user client may be further adapted to alert the user of an unscheduled access attempt if the user client receives an access alert from the security band occurring outside a scheduled dose time. The user client may also be adapted to present the user with a dosage reminder notification if the security band does not transmit an access alert to the user client during the scheduled dose time.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 2A:
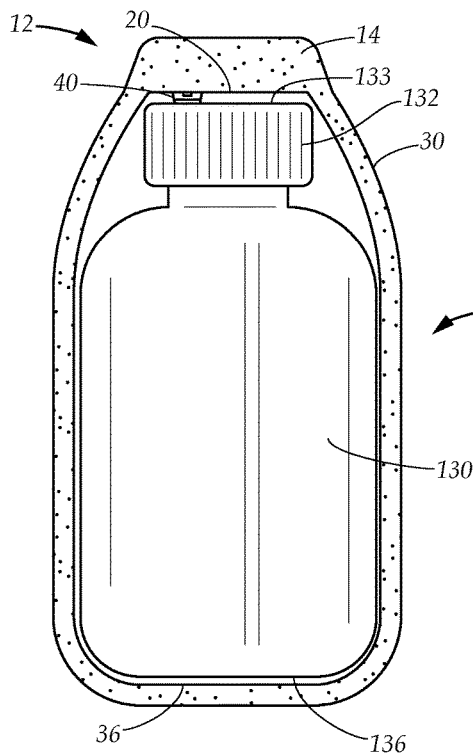
FIG. 2A is a front elevation view of the security band attached to the container in a securing position where the pressure switch within the hub is held in place against the lid of the container via the strap, in accordance with an embodiment of the present disclosure.
Figure 2B:
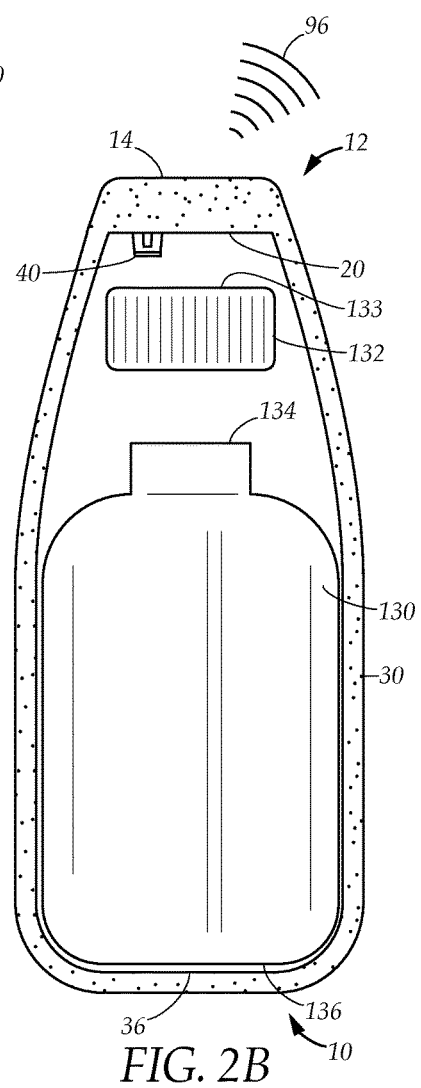
FIG. 2B is a front elevation view of the security band in a stretched state where the security band is stretched to allow the lid of the container to be removed.

FIGS. 2A-B illustrate a security band 10, attached onto a container 130. The container 130 defines an interior for storing contents therein, has a bottom 136, and has an opening 134 fully opposite from the bottom 136. A lid 132 is selectively attached onto the container 130 for preventing access to the interior of the container and its contents through the opening 134 when located thereupon. The lid has a top surface 133 disposed opposite from the opening 134.

Figure 1A:
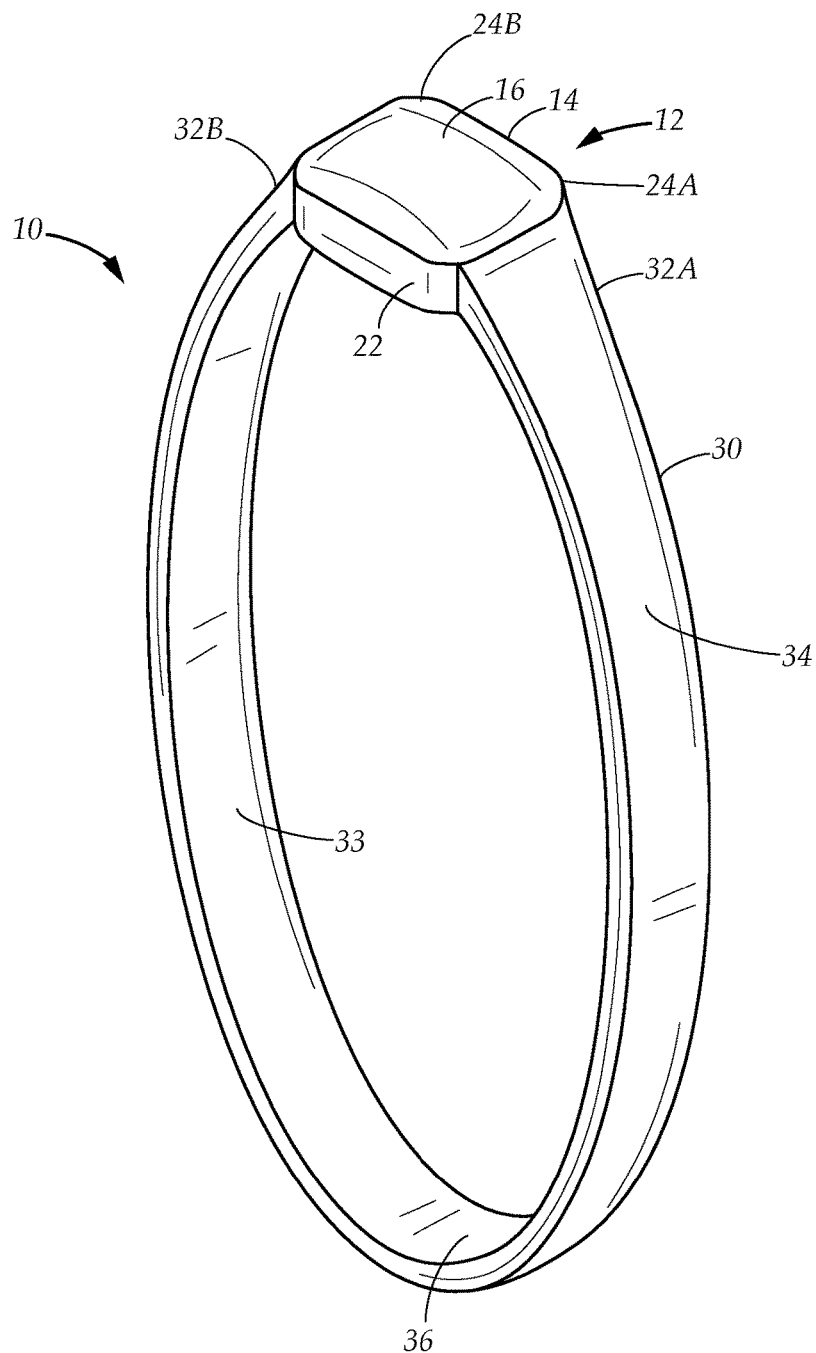
FIG. 1A is a diagrammatic perspective view depicting a security band having a hub and a strap, in accordance with an embodiment of the present disclosure.
Figure 1B:
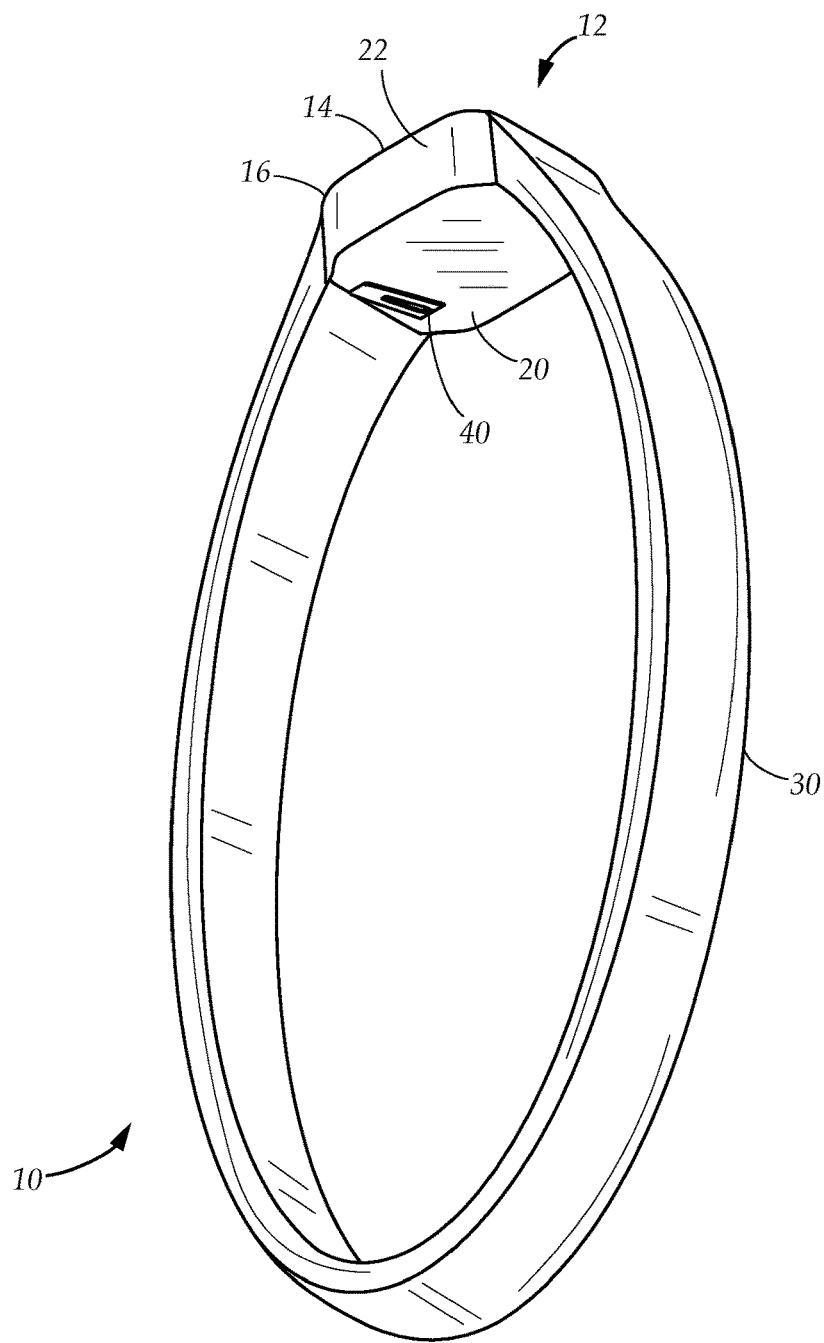
FIG. 1B is a diagrammatic perspective view depicting the security band from below, showing a pressure switch positioned on the hub, in accordance with an embodiment of the present disclosure.

Referring now to FIGS. 1A-B and 2A, the security band 10 comprises a hub 12 and a strap 30. The security band 10 securely attaches to the container 130, and prevents a user or other person from gaining access to the lid 132 without first removing or otherwise disturbing the security band. The security band 10 may function within a security band system comprising the security band and at least one user client. In a preferred embodiment, the security band 10 attaches to the container 130 in a securing position where the hub 12 covers the lid 132 of the container while the strap 30 wraps around the container and securely holds the hub 12 in place over the lid 132. The security band 10 further comprises at least one sensor disposed within the hub 12 or the strap 30, which is configured to detect the removal or disturbance of the security band. The security band 10 further comprises a control module, contained in the hub 12, through which the electronic functions of the security band 10 are implemented. The control module is also adapted to wirelessly communicate with the user client. If the security band 10 is removed from the container or disturbed, the control module may wirelessly transmit an access alert signal to a user via the user client. In a preferred embodiment, the security band 10 may be used to secure the lid of a container holding medication in order to detect unauthorized or unscheduled access to the medication. The user may be a patient for whom the medication within the container is intended, a caretaker responsible for the patient, a health professional, or any person tasked with overseeing access to the contents of the container. The container may be a typical jar, vial, or bottle commonly used for holding medications. The lid may be a screw top lid, a child resistant push and turn cap, hinged lid, or any other commonly used closure type.

The hub 12 comprises a housing 14 having an upper surface 16, a lower surface 20, a first connecting end 24A, and a second connecting end 24B. The housing 14 may further comprise a housing cavity which encloses the control module. The housing 14 may be formed in any shape and size suitable for covering the lid 132. For example, the housing 14 may be substantially circular or rectangular, and in certain embodiments, the housing may further comprise a pair of longitudinal surfaces 22. In a preferred embodiment, the strap 30 comprises an elastic strip having an inner surface 33, an outer surface 34, a first end 32A and a distally disposed second end 32B. The strap 30 further has a central point 36 located on the inner surface 33 approximately midway between the first and second ends 32A, 32B. The first end 32A of the strap 30 is attached to housing 14 at the first connecting end 24A, while the second end 32B is attached to the second connecting end 24B.

The strap 30 is preferably formed from an elastic material with high frictional properties such as rubber or other type of elastomer. High friction allows the inner surface 33 of the strap 30 to frictionally grip the container 130, causing the security band 10 to be more securely attached to the container by preventing slippage of the strap 30. The housing 14 may also be formed from material similar to that of the strap 30. In certain embodiments, the housing 14 and the strap 30 may be formed from a substantially continuous piece of material. To prevent the housing 14 from deforming under stress as the security band is handled or stretched, which may cause the control module to become damaged or unseated within the housing cavity, the housing may be reinforced with a frame of metal, plastic, or other similar rigid material. In other embodiments, the housing 14 may instead be formed from metal, plastic, or other rigid material. The strap 30 and the housing 14 may therefore be formed instead as separate components.

Turning now to FIGS. 2A-B, while continuing to refer to FIGS. 1A-B, the security band 10 may be attached to the container 130 in the securing position by first placing the lower surface 20 of the housing 14 in contact with the top surface 133 of the lid 132, and then wrapping the strap 30 around the bottom 136 of the container 130 so that the central point 36 of the strap 30 contacts the bottom 136. In a preferred embodiment, when the security band 10 is in a relaxed condition, the inner surface 33 of the strap 30 and the lower surface 20 of the housing form an elliptical shape which has a diameter less than the height of the container 130 as measured from the bottom 136 to the top surface 133 of the lid 132. Therefore, in order for the security band 10 to be attached to the container 130, the strap 30 must be stretched to adapt to the height of the container. This provides tension, which holds the lower surface 20 of the housing 14 in place against the top surface 133 of the lid 132. While the hub 12 remains in place over the lid 132, the user or other person cannot gain access to or remove the lid 132 without first stretching the security band 10 and breaking the contact between the lower surface 20 of the housing 14 and the lid 132.

In a preferred embodiment, the sensor may be a pressure switch 40 positioned upon the lower surface 20 of the housing 14. When the security band 10 is attached to the container, the pressure switch 40 comes into contact with the top surface 133 of the lid and enters into an engaged state. When the security band is stretched or removed, the lower surface 20 of the housing 14 separates from the top surface 133 of the lid 132, and the pressure switch 40 enters into a disengaged state. In alternate embodiments, there may be an intervening structure positioned between the pressure switch 40 and the lid 132. In such embodiments, the lid applies pressure to the pressure switch through the intervening structure. This change in state from the engaged to the disengaged state indicates the occurrence of an access event, and the security band 10 may then wirelessly transmit an access alert signal 96 to the user client indicating access to the lid by the user or other person.

Figure 2C:
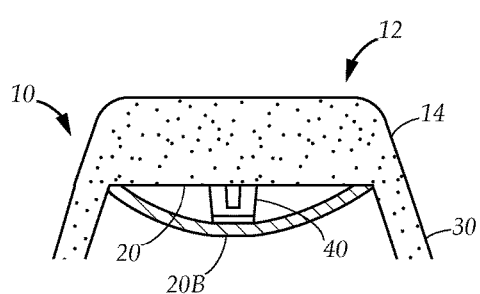
FIG. 2C is a partial cross section view of the security band, depicting a lower elastic layer which covers the pressure switch, in accordance with an embodiment of the present disclosure.

Referring to FIG. 2C while continuing to refer to FIGS. 2A-B, in certain embodiments, the housing 14 may further comprise a lower elastic layer 20B which covers the pressure switch 40 and may also cover the lower surface 20. Rather than contacting the pressure switch 40 and the lower surface 20 directly, the top surface 133 of the lid 132 first contacts the lower elastic layer 20B. The lower elastic layer 20B is formed from a soft, elastic material, such as silicone, which does not interfere with the operation of the pressure switch 40 and allows the pressure switch 40 to be engaged and disengaged through the elastic material of the lower elastic layer 20B.

Figure 3:
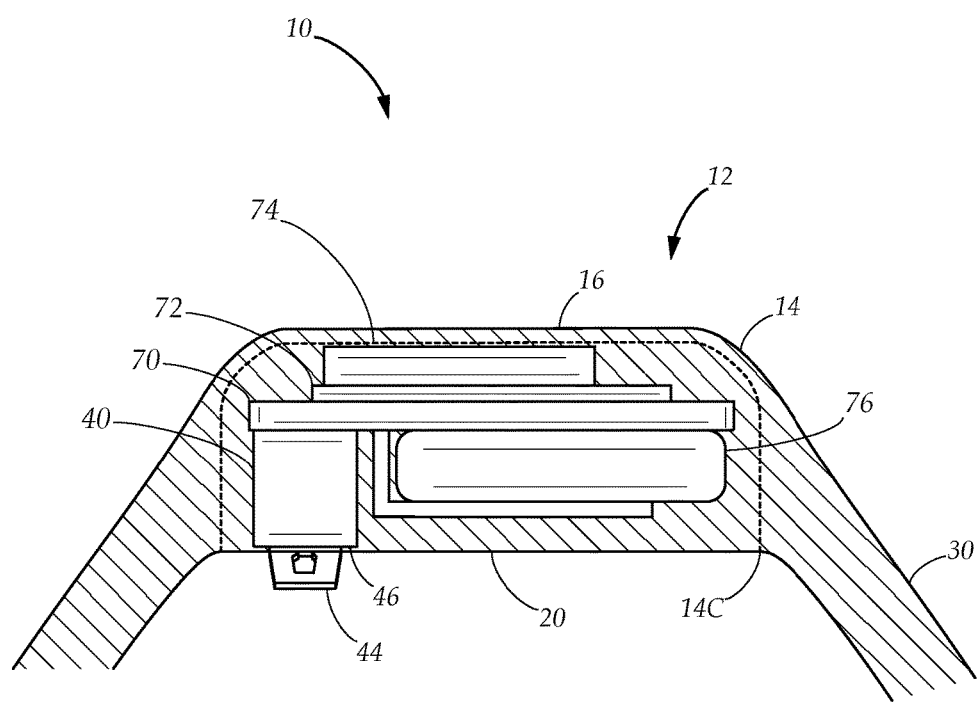
FIG. 3 is a diagrammatical cross section view of the hub of the security band revealing a control module, in accordance with an embodiment of the present disclosure.
Figure 4:
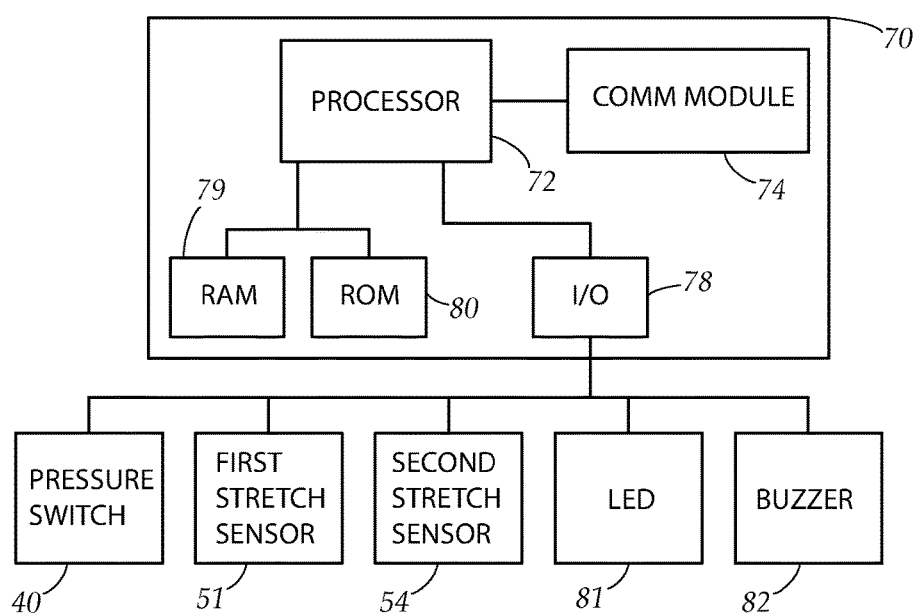
FIG. 4 is a block diagram depicting the control module, in accordance with an embodiment of the present disclosure.

Turning now to FIGS. 3 and 4, while continuing to refer to FIGS. 2A-B, the control module 70 is preferably enclosed within the housing cavity 14C formed within the housing 14. The control module comprises a processor 72, a RAM 79, a ROM 80, and a communication module 74. The communication module 74 incorporates an RF transceiver capable of receiving and transmitting data via Bluetooth, WIFI, or other wireless communication technology. The control module may further have one or more input/output ("I/O") ports 78, which are operably connected to the one or more sensors, such as the pressure switch 40. In a preferred embodiment, the control module 70 may be implemented using a system-on-chip ("SOC"). The hub 14 may also have an LED 81 and/or a buzzer 82 operably connected with the control module 70, which are adapted to convey audio and visual alerts to the user. For example, the LED may flash, and/or the buzzer may emit a tone, when the security band 10 detects the occurrence of an access event. The control module 70 and the sensors may be powered by a battery 76, which can either be a rechargeable battery, or a user-replaceable battery such as a coin-cell battery.

In a preferred embodiment, the pressure switch 40 comprises a lever arm 44 and a contact surface 46. The lever arm 44 may be implemented as a metal spring arm which projects away from the lower surface 20 of the housing 14. The contact surface 46 is positioned on the lower surface 20 of the hub such that the lever arm 44 bends when subjected to pressure and touches the contact surface 46. Once the lever arm 44 touches the contact surface 46, a conductive contact is established and the pressure switch 40 enters the engaged state. Releasing the pressure upon the lever arm 44 causes the lever arm to return to its original position, breaking the conductive contact with the contact surface 46 and causing the pressure switch 40 to enter the disengaged state. In other embodiments, the pressure switch may be implemented using a spring-loaded push button switch, or any other mechanism or sensor which is commonly employed to detect pressure.

The control module 70 detects the change between the engaged and disengaged states and responds accordingly. In a preferred embodiment, the control module 70 may operate in a low-power mode while the pressure switch 40 is engaged. When the pressure switch 40 enters the disengaged state, the control module 70 may interpret the state change as the occurrence of an access event, and then enter an active power mode. The control module 70 may then activate the communication module 74, establish a wireless connection to the user client, and transmit the access alert to the user client. Operating in the low power mode allows the control module 70 to conserve battery power by becoming active only when the safety band 10 is disturbed and/or the hub 12 is detached from the lid 132 of the container 130.

Figure 5A:
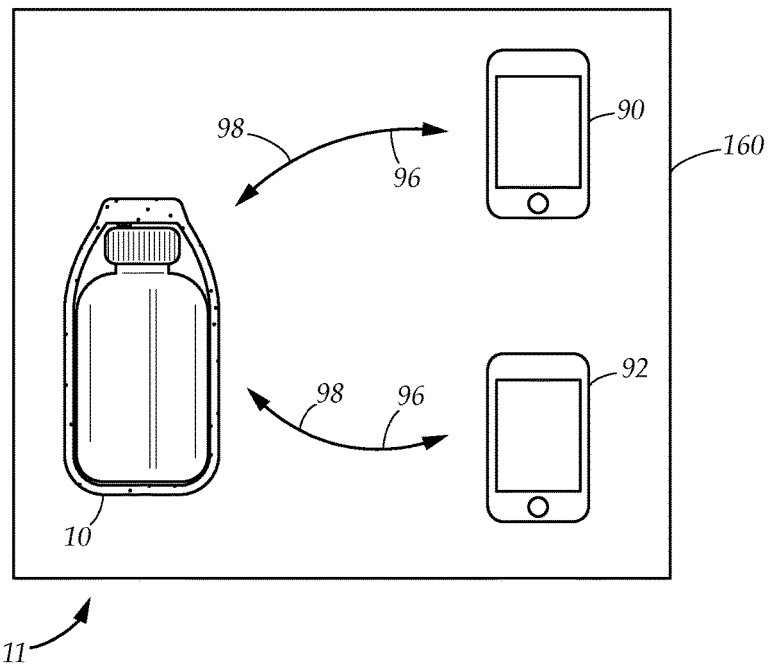
FIG. 5A is a block diagram depicting the security band in communication with a security band system, in accordance with an embodiment of the present disclosure.
Figure 5B:
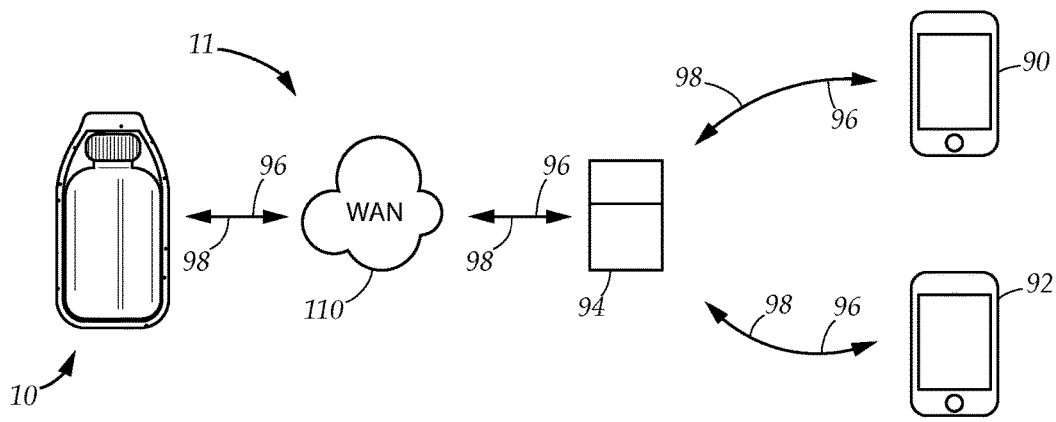
FIG. 5B is a block diagram depicting the security band in communication with a control server via a LAN/WAN, in accordance with an embodiment of the present disclosure.

Turning now to FIGS. 5A-B while simultaneously referring to FIGS. 3 and 4, the security band 10 may be configured to wirelessly communicate with the user client 90 using a short-ranged transmission technology such as Bluetooth. Alternatively, the security band 10 may communicate with the user client 90 via a shared local area network ("LAN"), which the security band 10 may connect to via WIFI. In a preferred embodiment, the user client 90 can be a mobile phone, smartphone, tablet, PC, or other personal computing device. The user client 90 receives access alerts 96 transmitted by the security band 10, and may also transmit control signals 98 to the security band. The user client 90 may comprise a display and/or a speaker, allowing the user client to notify the user of access alerts or other events using visual or audio cues via the display and/or the speaker. The security band system 11 may further comprise a second user client 92, which performs the same functions as the user client 90 and allows more than one user to receive access alerts 96 from the security band. For example, the user client 90 and the second user client 92 may be utilized by the patient and the caretaker respectively.

In certain embodiments, the security band system 11 may further comprise a control server 94 which is accessible to the security band 10 and the user client 90 via the LAN or a WAN 110 such as the Internet. The control server 94 facilitates communication between the security band 10 and the user client 90 via the WAN 110, and allows the security band 10 and the user client 90 to communicate when the user client 90 is not located in the same location 160 as the security band 10, or if the distance between the user client 90 and the security band exceeds the range of short-ranged transmissions. For example, if the security band 10 detects the occurrence of an access event while the user is away from home, the security band 10 may transmit the access alert 96 to the control server 94, and the control server 94 then relays the access alert to the user client 90.

A control application implemented on the user client 90 and/or the control server 94 may be adapted to receive and interpret access alerts and other signals from the security band 10. In a preferred embodiment, the control application may perform a scheduled access check by comparing the time which each access alert 96 is received by the user client 90 and/or the control server 94 with a dosage schedule. The dosage schedule may contain a list of scheduled dose times and/or dosage frequencies which govern the proper consumption of the medication by the patient. If the control application receives an access alert 96 which deviates from the dosage schedule, the control application may notify the user of an unscheduled access alert via the user client 90. The control application may also notify the user via the user client if the patient misses a scheduled dose. In certain embodiments, the dosage schedule may be stored within the control module 70 of the security band itself, and the control module 70 may be further adapted to perform scheduled access checks. The control application may also be used to configure the security band 10, such as by setting up network access, programming the dosage schedule, inputting user information, and configuring other options as will be apparent to a person of ordinary skill in the art in the field of the invention.

Figure 6:
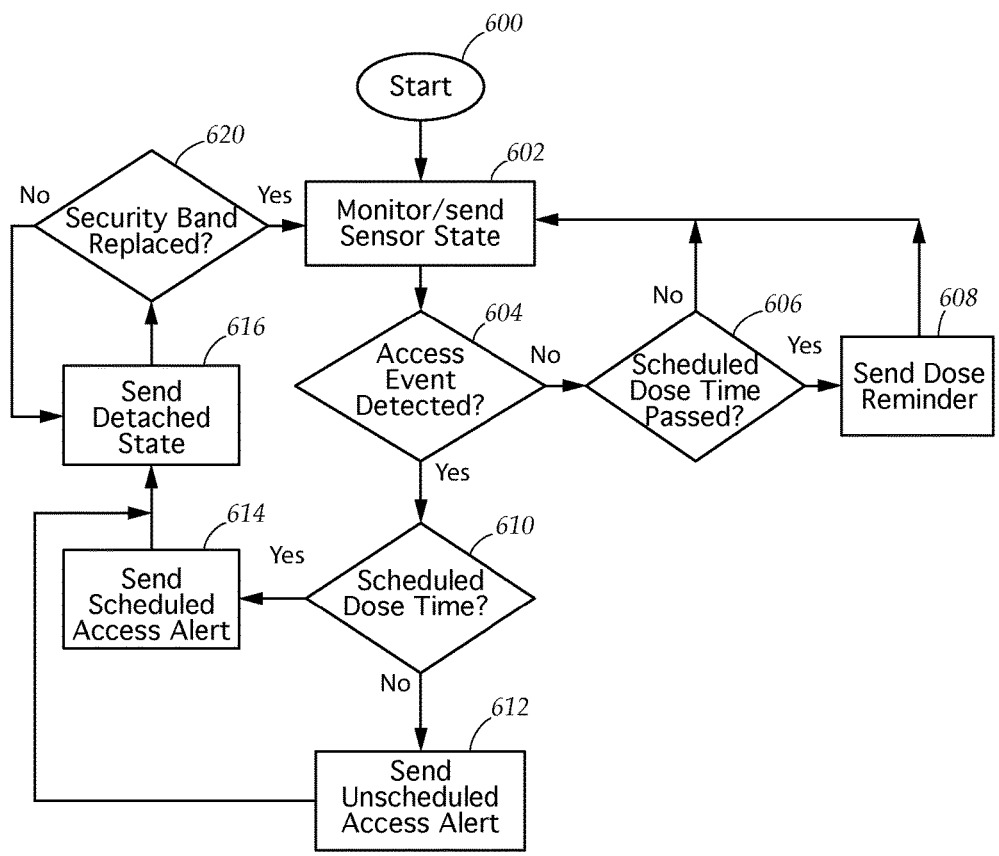
FIG. 6 is a flowchart depicting an exemplary access detection process, in accordance with an embodiment of the present disclosure.

Turning now to FIG. 6, while simultaneously referring to FIGS. 2A-B, FIG. 4, and FIGS. 5A-B, an exemplary access detection process begins at step 600, when the security band 10 is attached to the container 130 in the securing position. Although the access detection process utilizes the functions of both the security band 10 and the control application as implemented on the user client 90 or the control server 94, it may be possible for certain functions of the control application to be implemented using the control module 70 instead. In a preferred embodiment, the security band 10 enters into an access detection mode when the pressure switch 40 enters into the engaged state. The process then proceeds to step 602, where the control module 70 monitors the pressure switch 40 for a change in state. In some embodiments, the control module 70 may operate in a continuous power mode and maintain an active wireless connection to the user client 90 and/or the control server 94. While so connected, the control module 70 may transmit a state signal to the control application indicating the present state of the pressure switch. Alternatively, if the control module 70 is operating in the low power mode, the control module may remain disconnected from the user client 90 and/or control server 94 to conserve power until the occurrence of an access event.

Next, the process proceeds to step 604, and the security band system determines whether an access event has occurred. In a preferred embodiment, if the control application does not receive an access alert from the security band at step 604, the process proceeds to step 606 and the control application may check the dosage schedule to determine if a scheduled dose time has passed. If the scheduled dose time has passed, the process then proceeds to step 608 and the control application may send a dose reminder notification to the patient via the user client 90. If the scheduled dose time has not passed, the process may then return to step 602.

However, if the control module 70 detects the occurrence of an access event at step 604, the control module 70 transmits an access alert to the user client 90 and/or control server 94, and the process proceeds to step 610. At step 610, the control application performs a scheduled access check to determine whether the access event occurred during a scheduled dose time. The scheduled dose time may be a specific time, or a time window. If the access event occurred outside of the scheduled dose time, the process proceeds to step 612 and the control application notifies the user of an unscheduled access alert via the user client 90. In certain embodiments, the control application may also send a control signal 98 to the security band to cause the LED 81 within the hub 12 to flash a warning, and/or cause the buzzer 82 to emit a warning tone. If the access event occurred during the scheduled dose time, the process proceeds to step 614 and the control application notifies the user of a scheduled access event via the user client 90.

In certain embodiments, the security band 10 may notify the control application if the security band is not repositioned on the container within a certain time interval following the occurrence of the access event. This time interval may, for example, be from one to five minutes, or any length of time which would reasonably allow the patient to reposition the security band 10 over the container 130 after removing the medication for the scheduled dose. Following the completion of steps 612 or 614, the access detection process may proceed to step 616 where the security band signals the control application indicating the security band is in a detached state. Once the time interval for repositioning has elapsed, the process may then proceed to step 620. At step 620, if the control module 70 continues to indicate that the security band 10 is in the detached state, the process then returns to step 616 and the control application may notify the user via the user client 90 that the security band 10 remains detached. However, if the control module 70 indicates that the pressure switch has returned to the engaged state, the process then returns to step 602 and the security band resumes monitoring the state of the pressure switch 40 in advance of the next scheduled dose.

Note that the exemplary access detection process is non-limiting, and the steps of the process may be added, removed, or varied as necessary, in adherence with the principles of the present disclosure. For example, the security band system may be configured so that any change in the state of the pressure switch 40 from the engaged to disengaged state results in an unauthorized access alert, representing an alternate use scenario where the security band is employed to secure medication kept in storage which is not intended for consumption. The access detection process may also be adapted to function with sensor types other than the pressure switch 40.

Figure 7A:
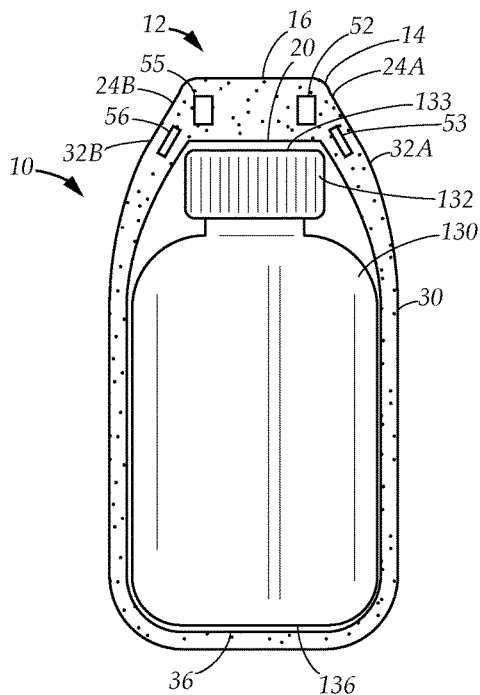
FIG. 7A is a front elevation view of a security band equipped with stretch sensors, in accordance with an embodiment of the present disclosure.
Figure 7B:
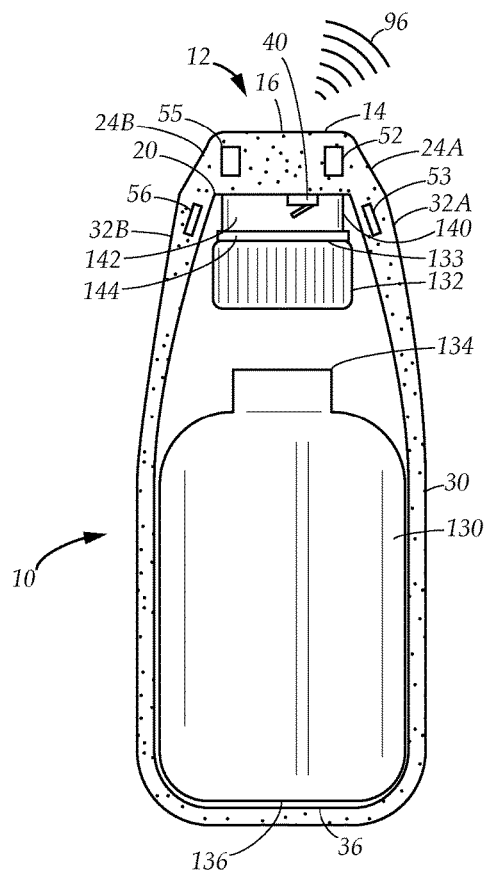
FIG. 7B is a front elevation view of the security band equipped with stretch sensors, depicting the strap in an elongated stretched position.

Turning now to FIGS. 7A-7B, while also referring to FIGS. 2A-B and FIG. 4, alternative embodiments may incorporate additional sensors and structures in addition to, or in place of, the pressure switch 40. For example, such additional sensors may detect an access event by determining when the strap 30 has been stretched to initiate removal of the cap 132 from the container 130. In one embodiment, the security band 10 may further comprise a first stretch sensor 51 and a second stretch sensor 54 adapted to measure tension within the strap 30 as it stretched. The first and second stretch sensors 51, 54 are operably connected to the control module 70 such that the security band 10 registers an access event when the strap is stretched. In certain embodiments, the first and second stretch sensors 51, 54 may be positioned between the first connecting end 24A of the housing and the first end 32A of the strap 30, and between the second connecting end 24B of the housing and the second end 32B of the strap 30 respectively. The first and second stretch sensors 51, 54 may alternatively be implemented using a first hall effect sensor 52 and a first magnet 53, and a second hall effect sensor 55 and second magnet 56. The first and second hall effect sensors 52, 55 may be positioned at the first and second connecting ends 24A, 24B of the housing 14, while the first and second magnets 53, 56 may be positioned at the first and second ends 32A, 32B of the strap respectively. The first and second hall effect sensors 52, 55 are each adapted to generate an output signal when exposed to magnetic fields produced by the first and second magnets 53, 56. The strength of the output signal is inversely proportional to the distance between the hall effect sensor and the corresponding magnet. As the security band 10 is stretched, the strap 30 becomes elongated and the distance between the first and second hall effect sensors 52, 55 and the first and second magnets 53, 56 increases, causing the strength of the output signals to diminish. In one embodiment, the strength of the output signals may correspond to a plurality of tension states, comprising a secured state and a stretched state, which reflect the degree of elongation of the strap 30, or the amount of tension within the strap, as it stretched or relaxed. The strength of the output signals when the security band 10 is attached to the container 130 in the securing position may correspond to the secured state. As the strap 30 is stretched, the diminished strength of the output signals may correspond to the stretched state. The control module 70 receives the output signal from each of the first and second hall effect sensors 52, 55 and monitors the tension state of the strap 30. When the tension state changed from the secured state to the stretched state, the control module 70 may then register that an access event has occurred. In certain embodiments, the plurality of tension states may further comprise a relaxed state. When the security band 10 is completely detached from the container 130, the strap 30 relaxes and the distance between the first and second hall effect sensors 52, 55 and the first and second magnets 53, 56 decreases, increasing the strength of the output signals. The control module 70 may further register an access event when the tension state of the strap 30 enters the relaxed state. This feature may be used to detect separation of the security band 10 from the container in cases where the strap 30 is slipped sideways off the container without being stretched. Note that the stretch sensors may be implemented using other types of sensors. In alternate embodiments, a strain gauge, a variable resistance stretch sensor, or other type of sensor may be employed to measure the tension state of the strap 30.

In certain embodiments, the security band 10 may utilize the stretch sensors in place of the pressure switch. Returning to FIG. 6, while also referring to FIGS. 2A-B, 4, and 7A-B, the access detection process may begin at step 600 when the control module 70 detects that the tension state of the strap 30 is in the secured state. The secured state may correspond to the strength of the output signals produced by the stretch sensors when the security band is attached to the container 130 in the securing position, where the lower surface 20 of the housing 14 is positioned in contact with the lid 132 and the central point 36 of the strap 130 is wrapped around the bottom 136 of the container 130. For purposes of the access detection process, the secured state and stretched state may correspond to the engaged and disengaged states of the pressure switch, and the control module 70 may detect the occurrence of an access event if the tension state of the strap 30 changes from the secured state to the stretched state. Therefore, at steps 602, 616, and 620, the control module 70 may monitor the stretch sensors for a change in the tension state of the strap 30. In other embodiments, the stretch sensors may be utilized in combination with the pressure switch. For example, in a preferred embodiment, the security band 10 may employ the first and second hall effect sensors 52, 55, in conjunction with the pressure switch 40. The pressure switch may be employed to begin the access detection process and/or to detect access events. Utilizing both the pressure switch 40 to detect the separation of the hub 12 from the lid 132, and the stretch sensors to detect changes in the tension state of the strap 30, increases the reliability of the security band 10 and further allows the security band 10 to resist attempts by a person to circumvent either the stretch sensors or the pressure switch.

Returning to FIG. 7B, in an alternate embodiment, the security band may further comprise an extension mechanism 140. The pressure switch 40 may be supplemented by the extension mechanism 140, which projects away from the lower surface of the housing 14. The extension mechanism 140 comprises an extension segment 142, which may be a substantially hollow polygonal or circular tube, as well as a substantially planar extension surface 144 which is formed across the end of the extension segment located away from the housing 14. The extension segment further surrounds the pressure switch 40. The extension mechanism 140 may be spring-actuated such that the extension segment 142 retracts into the hub 12 when pressure is applied to the extension surface 144, and extends out of the hub 12 when the pressure abates. As the extension segment 142 retracts, the extension surface 144 contacts the pressure switch 40 and causes the pressure switch to enter the engaged state, whereas the contact between the pressure switch 40 and the extension surface 144 is broken once the extension segment extends, causing the pressure switch 40 to enter the disengaged state. The extension surface 144 may be any size, and can have an area which is either lesser, equal to, or greater than the area of the lower surface 20 of the housing 14. This allows the extension surface 144 to contact a lid 132 of any size and shape, and makes it unnecessary for the user to adjust the position of the hub 12 to ensure that the pressure switch 40 contacts the lid 132.

Figure 8:
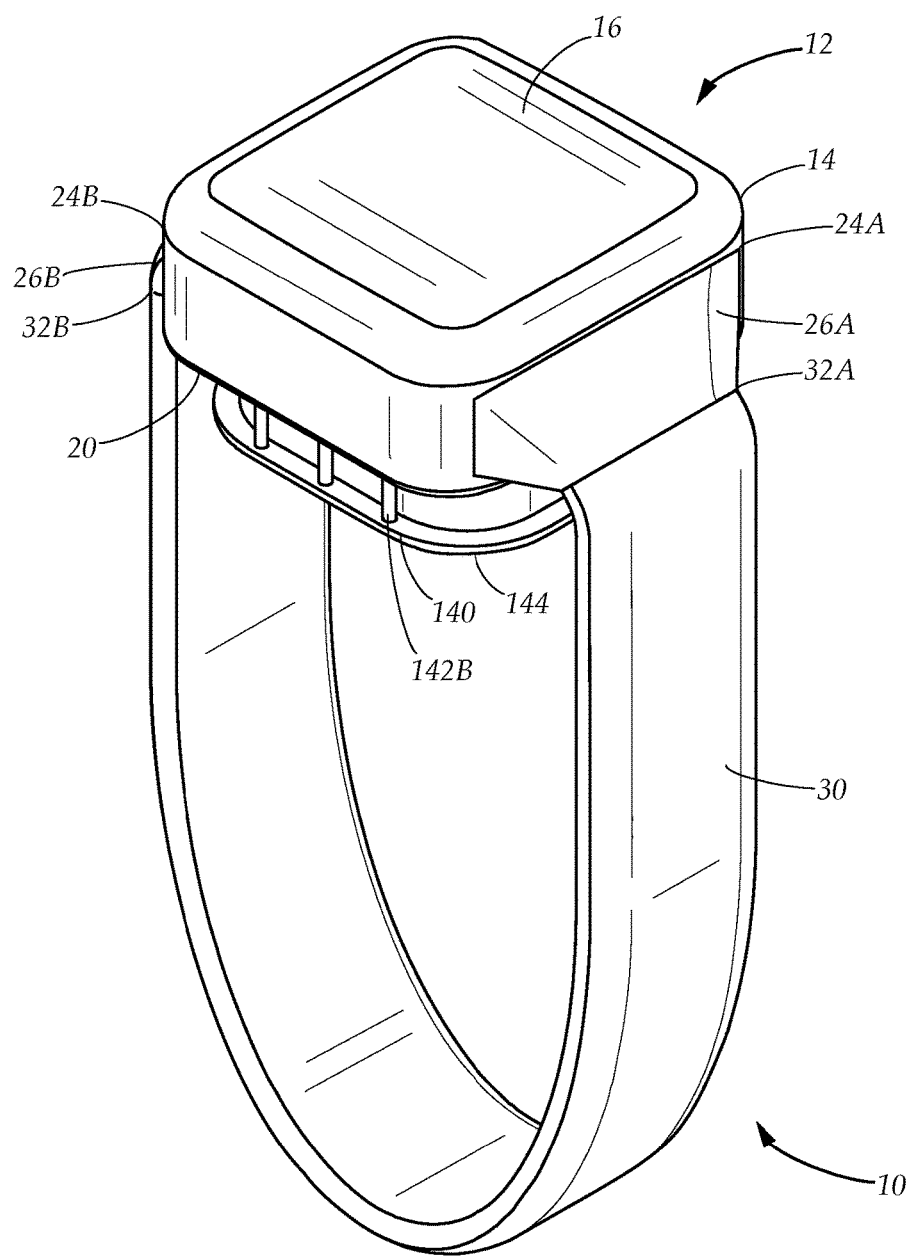
FIG. 8 is a diagrammatic perspective view depicting a security band equipped with an extension mechanism and a first and second connecting members, in accordance with an embodiment of the present disclosure.
Figure 9:
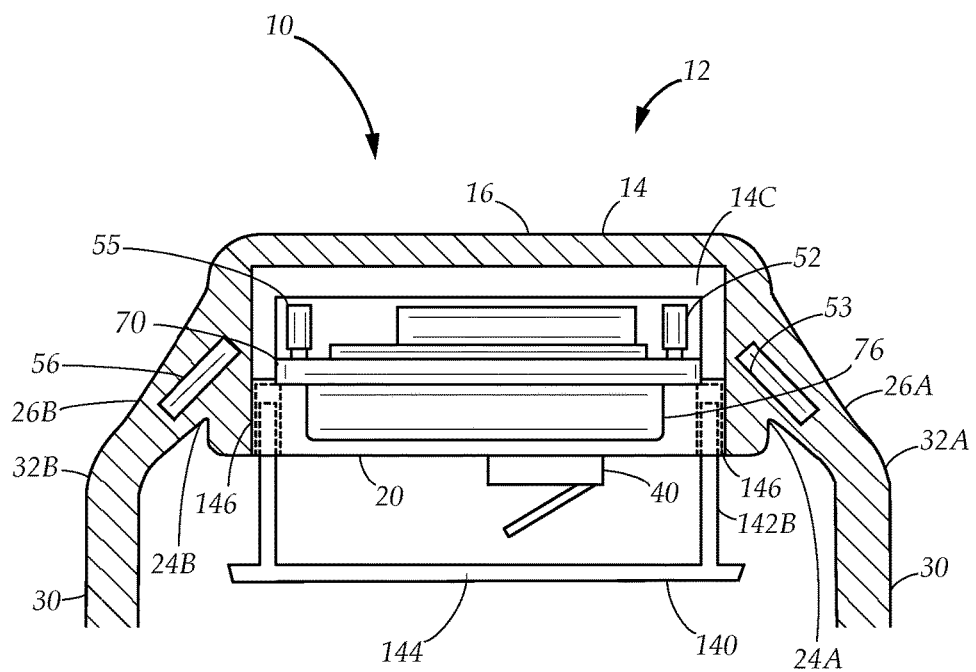
FIG. 9 is a cross sectional view of the security band, further detailing the extension mechanism, while also showing the positioning of first and second hall effect sensors in relation to first and second magnets, in accordance with an embodiment of the present disclosure.

Turning now to FIGS. 8 and 9, while continuing to refer to FIG. 7B, in certain embodiments, the extension segment 142 may alternatively be formed as a plurality of rods 142B, instead of as a continuous tube. Each rod 142B may be spring-actuated and retained within an extension recess 146 formed within the hub 12. In other embodiments, the extension mechanism 140 may be utilized in place of the pressure switch 40, to fulfil substantially the same function as the pressure switch 40. When the extension segment 142 retracts and extends, the control module 70 may register that the extension mechanism 140 is in the engaged and disengaged states respectively.

Figure 7C:
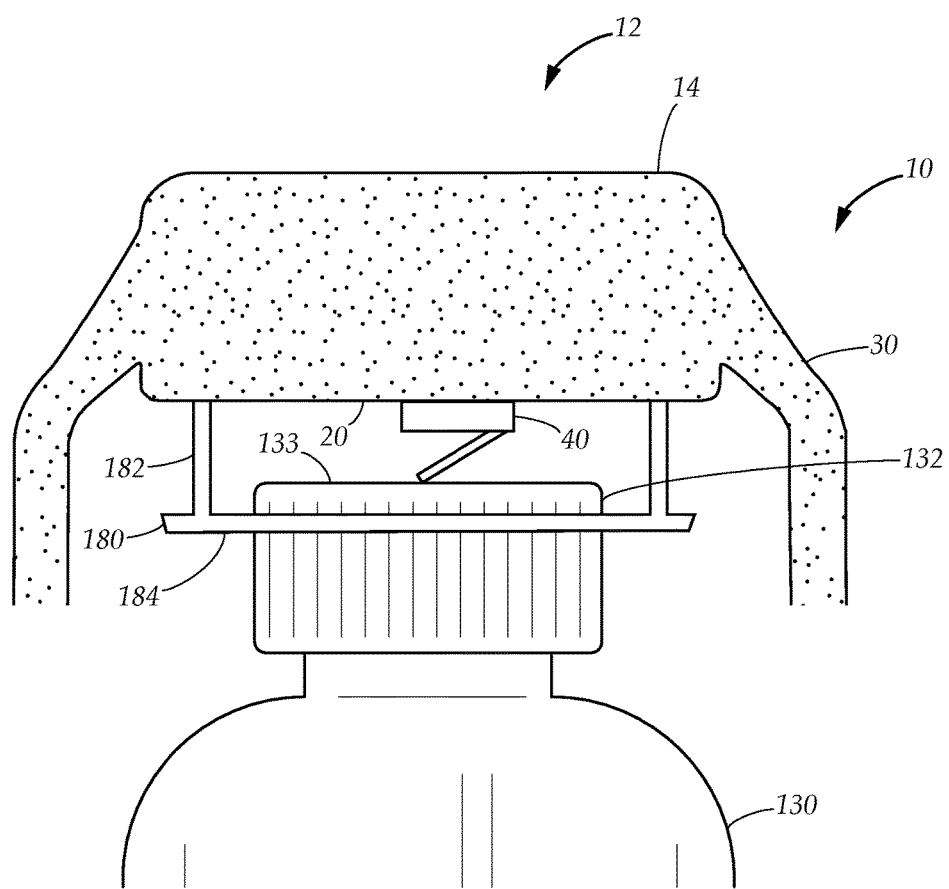
FIG. 7C is cross sectional view of a security band equipped with a lip guard which surrounds the lid of the container, in accordance with an embodiment of the present disclosure.

Referring now to FIG. 7C, the hub 12 may further comprise a lid guard 180 which projects from the lower surface 20 of the housing 14. The lid guard 180 comprises a substantially hollow guard extension 182 which can be formed as a tube with a polygonal or circular cross-sectional shape, or as a plurality of guard segments. The lid guard 180 may further comprise a guard lip 184 positioned at an open end of the guard extension 182 disposed away from the housing 14. The open end of the guard extension 182 and/or the guard lip 184 are sized to receive and enclose the lid 132 of the container 130, so that the lid guard 180 surrounds the lid 132 when the security band 10 is attached to the container 130 in the securing position, while allowing the top surface 133 of the lid 132 to contact the pressure switch 40. In the event that a person attempts to circumvent the pressure switch 40 by inserting a flat object in between the lid 132 and the pressure switch 40, the lid guard 180 would prevent such circumvention.

Returning to FIG. 9 while also referring to FIG. 8, in an alternate embodiment, the security band 10 may have a modular design where the control module 70 is removably contained within the housing 14, so that the control module 70 to be removed from within the housing cavity 14C to be inserted into a different hub and strap combination. This allows the security band 10 to adapt to a variety of containers by pairing the control module 70 with a strap 30 of the appropriate length and a hub 12 of the appropriate size and shape.

In certain embodiments, such as when the housing 14 and the strap 30 are formed as separate components or when the control module 70 is removable from within the housing 14, the first and second hall effect sensors 52, 55 may be located on the control module 70 in positions proximate to the first and second connecting end 24A, 24B of the housing 14, while the first and second magnets 53, 56 may be positioned within the strap 30 at the first and second connecting ends 24A, 24B respectively.

Returning to FIG. 8 while also referring to FIG. 9, in embodiments where the housing 14 and the strap 30 are formed as separate components, the housing 14 may further comprise a first connecting member 26A which projects from the first connecting end 24A of the housing 14, and a second connecting member 26B which projects from the second connecting end 24B of the housing 14. The first and second connecting members 26A, 26B may enclose and elastically retain the first and second ends 32A, 32B of the strap 30 in positions proximate to the first and second connecting ends 24A, 24B of the housing 14. When the strap 30 is stretched, the first and second ends 32A, 32B may separate from the first and second connecting ends 24A, 24B of the housing while remaining elastically retained within the first and second connecting members 26A, 26B. When the strap 30 is restored to its relaxed condition, the first and second connecting members 26A, 26B elastically return the first and second ends 32A, 32B of the strap 30 to their original positions proximate to the first and second connecting ends 24A, 24B of the housing 14. The first and second connecting members 26A, 26B therefore provide an efficient mechanism by which variations in distance between the first and second hall effect sensors 52, 55 and the first and second magnets 53, 56 in response to the stretching and relaxation of the strap 30 can be used to detect the plurality of tension states.

Note that further variations and combinations are possible, which have not been expressly discussed in the present disclosure. A person of ordinary skill in the art in the field of the invention will appreciate that the described variations of the housing, strap, pressure switch, stretch sensors, and other structures described herein can be utilized in other combinations, in adherence with the principles of the present disclosure.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate or transport a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. Other types of languages include XML, XBRL and HTML5. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. Each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments of the present disclosure. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The flow diagrams depicted herein are just one example. There may be many variations to this diagram or the steps (or operations) described therein without departing from the spirit of the disclosure. For instance, the steps may be performed in a differing order and/or steps may be added, deleted and/or modified. All of these variations are considered a part of the claimed disclosure.

In conclusion, herein is presented a security band for securing and detecting access to a container. The disclosure is illustrated by example in the drawing figures, and throughout the written description. It should be understood that numerous variations are possible, while adhering to the inventive concept. Such variations are contemplated as being a part of the present disclosure.

What is claimed is:

1. A security band for securing a container containing medication as well as communicating with a user client device, the container having a bottom, an opening, and a lid which covers the opening, the security band comprising:
 a hub comprising a housing having an upper surface, a lower surface, a first connecting end and a second connecting end, the housing further comprises a housing cavity formed between the upper surface and lower surface;

a strap comprising an elastic strip having an inner surface and an outer surface, the strap further comprises a first end attached to the first connecting end of the housing, a second end attached to the second connecting end of the housing, and a central point located on the inner surface approximately midway between the first end and the second end;

a pressure switch positioned on the lower surface of the housing;

a control module contained within the housing cavity, the control module comprises a processor and a communication module, and is adapted to wirelessly communicate with the user client device;

wherein the security band is adapted to securely attach to the container in a securing position which prevents the lid of the container from opening, wherein the lower surface of the housing contacts the lid of the container while the strap wraps around the container such that the central point of the strap contacts the bottom of the container;

wherein attaching the security band to the container in the securing position places the pressure switch in contact with the lid, causing the pressure switch to enter an engaged state, whereby removal of the security band from the securing position breaks the contact between the pressure switch and the lid, causing the pressure switch to enter a disengaged state; and wherein the control module is adapted to detect an occurrence of an access event when the pressure switch enters into the disengaged state from the engaged state, and the control module is further adapted to transmit an access alert signal to the user client device upon detecting the access event, notifying a user of the removal of the security band from the securing position.

2. The security band as described in claim 1, wherein the security band further comprises a first stretch sensor positioned between the first connecting end of the housing and the first end of the strap, and a second stretch sensor positioned between the second connecting end of the housing and the second end of the strap, wherein the first and second stretch sensors are adapted to detect a plurality of tension states reflecting tension within the strap as the strap is alternatively stretched or relaxed, the plurality of tension states comprising a secured state and a stretched state, wherein the tension state of the strap corresponds to the secured state when the security band is attached to the container in the securing position, and the tension state of the strap corresponds to the stretched state when the strap is stretched to release the security band from the securing position; and wherein the control module is further adapted to detect the occurrence of the access event when the tension state of the strap begins in the secured state and then transitions to the stretched state.

3. The security band as described in claim 2, wherein the hub further comprises a lid guard which projects from the lower surface of the housing, the lid guard comprises a substantially hollow guard extension, the guard extension having an open end sized to receive the lid of the container, such that the lid guard surrounds the lid when the security band is attached to the container in the securing position.

4. The security band as described in claim 3, wherein the plurality of tension states further comprise a relaxed state, wherein the tension state of the strap corresponds to the relaxed state when the security band is detached from the container; and wherein the control module is further adapted to detect the occurrence of the access event when the tension state of the strap begins in the secured state or the stretched state and then transitions to the relaxed state.

5. The security band as described in claim 4, wherein the first stretch sensor comprises a first hall effect sensor positioned within the first connecting end of the housing and a first magnet positioned within the first end of the strap, and the second stretch sensor comprises a second hall effect sensor positioned within the second connecting end of the housing and a second magnet positioned within the second end of the strap.

6. The security band as described in claim 5, wherein the housing and the strap are formed from a substantially continuous piece of elastic material.

7. The security band as described in claim 6, wherein the control module is removably contained within the housing cavity, wherein the control module is adapted to be removed from within the housing cavity and inserted into a different hub and strap combination.

8. A security band for securing a container containing medication as well as communicating with a user client device, the container having a bottom, an opening, and a lid which covers the opening, the security band comprising:

a hub, the hub comprises a housing having an upper surface, a lower surface, a first connecting end and a second connecting end, the housing further comprises a first connecting member which projects from the first connecting end, a second connecting member which projects from the second connecting end, and a housing cavity formed within the housing between the upper surface and the lower surface;

a strap comprising an elastic strip having an inner surface, an outer surface, a first end, a second end, and a central point located on the inner surface approximately midway between the first end and the second end, the first connecting member encloses and elastically retains the first end of the strap in a position proximate to the first connecting end, and the second connecting member encloses and elastically retains the second end of the strap in a position proximate to the second connecting end;

a pressure switch positioned on the lower surface of the housing;

a first stretch sensor and a second stretch sensor, the first stretch sensor is positioned between the first connecting end of the housing and the first end of the strap and the second stretch sensor is positioned between the second connecting end of the housing and the second end of the strap, wherein the first and second stretch sensors are adapted to detect a plurality of tension states reflecting tension within the strap as it is stretched or relaxed, the plurality of tension states comprising a secured state and a stretched state;

a control module contained within the housing cavity, the control module comprises a processor and a communication module, and is adapted to wirelessly communicate with the user client device;

wherein the security band is adapted to securely attach to the container in a securing position which prevents the lid of the container from opening, wherein the lower surface of the housing contacts the lid of the container while the strap wraps around the container such that the central point of the strap contacts the bottom of the container;

wherein attaching the security band to the container in the securing position causes the lid to apply a pressure to the pressure switch, causing the pressure switch to enter an engaged state, whereby removal of the security band from the securing position releases the pressure of the lid against the pressure switch, causing the pressure switch to enter a disengaged state;

wherein the tension state of the strap corresponds to the secured state when the security band is attached to the container in the securing position, and the tension state of the strap corresponds to the stretched state when the strap is stretched to release the security band from the securing position;

wherein the control module is adapted to detect an occurrence of an access event when the pressure switch enters into the disengaged state from the engaged state or when the tension state of the strap begins in the secured state and transitions to the stretched state; and wherein the control module is further adapted to transmit an access alert signal to the user client device upon detecting the access event, notifying a user of the removal of the security band from the securing position.

9. The security band as described in claim 8, wherein the security band further comprises an extension mechanism, the extension mechanism projects away from the lower surface of the housing and comprises a substantially hollow extension segment which surrounds the pressure switch, and a planar extension surface parallel to the lower surface of the housing, the extension mechanism is spring-actuated and is further adapted to retract and extend within an extension recess formed within the hub; wherein the extension surface is adapted to contact the pressure switch and cause the pressure switch to enter the engaged state when the extension mechanism retracts, and break the contact with the pressure switch and cause the pressure switch to enter the disengaged state when the extension mechanism extends.

10. The security band as described in claim 9, wherein the plurality of tension states further comprise a relaxed state, wherein the tension state of the strap corresponds to the relaxed state when the security band is detached from the container; and wherein the control module is further adapted to detect the occurrence of the access event when the tension state of the strap begins in the secured state or the stretched state and transitions to the relaxed state.

11. The security band as described in claim 10, wherein the first stretch sensor comprises a first hall effect sensor positioned within the first connecting end of the housing and a first magnet positioned within the first end of the strap, and the second stretch sensor comprises a second hall effect sensor positioned within the second connecting end of the housing and a second magnet positioned within the second end of the strap.

12. The security band as described in claim 11, wherein the hub further comprises a lid guard which projects from the lower surface of the housing, the lid guard comprises a substantially hollow guard extension, the guard extension having an open end sized to receive the lid of the container, such that the lid guard surrounds the lid when the security band is attached to the container in the securing position.

13. The security band as described in claim 12, wherein the control module is removably contained within the housing cavity, wherein the control module is adapted to be removed from within the housing cavity and inserted into a different hub and strap combination.

14. A method for securing a container containing medication and detecting access to the container, the container having a bottom, an opening, and a lid which covers the opening, the method comprising the steps of:

providing a security band, the security band comprising:
a hub, a strap, and a control module, the hub comprises a housing, the housing comprising an upper surface, a lower surface, a first connecting end, and a second connecting end, the strap comprising an elastic strip having an inner surface, an outer surface, a first end attached to the first connecting end, a second end attached to the second connecting end, and a central point located on the inner surface approximately midway between the first end and the second end, the security band further comprising a pressure sensor positioned on the lower surface of the housing, wherein applying a pressure to the pressure switch causes the pressure switch to enter an engaged state and an absence of pressure causes the pressure switch to enter into a disengaged state, wherein the control module is operably connected to the pressure switch, the control module is adapted to wirelessly transmit an access alert signal;

providing a user client device, the user client device is adapted to receive the access alert signal from the control module;

securing the container by attaching the security band to the container in a securing position whereby the lower surface of the housing contacts the lid of the container while the strap wraps around the container such that the central point of the strap contacts the bottom of the container, the securing position prevents the lid from opening, wherein attaching the security band to the container in the securing position causes the lid to apply pressure to the pressure switch;

initializing an access detection mode, wherein the control module detects that the pressure switch enters the engaged state from the disengaged state, and initializes the access detection mode;

detecting an occurrence of an access event, wherein releasing the security band from the securing position causes the lower surface to break contact with the lid and further resulting in the absence of pressure from the lid against the pressure switch, causing the pressure switch to enter the disengaged state, wherein the control module detects the occurrence of the access event when the pressure switch enters into the disengaged state from the engaged state;

transmitting the access alert signal, wherein the control module transmits the access alert signal to the user client device upon detecting the occurrence of the access event; and notifying a user of an access alert by the user client device upon the user client device receiving the access alert signal.

15. The method as described in claim 14,
wherein the security band further comprises a first stretch sensor positioned between the first connecting end of the housing and the first end of the strap, and a second stretch sensor positioned between the second connecting end of the housing and the second end of the strap, wherein the first and second stretch sensors are adapted to detect a plurality of tension states reflecting tension within the strap as the strap is stretched or relaxed, the plurality of tension states comprising a secured state and a stretched state, wherein the control module is operably connected to the first and second stretch sensors;

wherein the step of securing the container by attaching the security band to the container in a securing position further comprises attaching the security band to the container in the securing position and causing the first and second stretch sensors to detect the secured state; and wherein the step of detecting the occurrence of an access event further comprises: wherein releasing the security band from the securing position causes the strap to stretch, causing the first and second stretch sensors to detect the stretched state, wherein the control module detects the occurrence of the access event when the tension state enters the stretched state from the secured state.

16. The method as described in claim 15, wherein the user client device further comprises a dosage schedule, the dosage schedule comprising a scheduled dose time window; and wherein the step of notifying a user of an access alert further comprises performing a scheduled dose check using the user client device to determine if the access event occurs outside the scheduled dose time window, and notifying the user of an unscheduled access alert when the access event occurs outside the scheduled dose time window.

17. The method as described in claim 16, the step of notifying a user of an access alert is followed by the step of presenting the user with a dosage reminder notification, wherein the user client device is adapted to present the user with the dosage reminder notification when the scheduled dose window elapses and no access alert signal is received by the user client device.

18. The method as described in claim 17, wherein:

the step of providing a user client device is followed by the step of providing a control server, the control server is adapted to communicate with the control module and the user client device via a wide-area-network; and the step of transmitting the access alert signal further comprises transmitting the access alert signal to the control server via the wide-area-network upon detecting the occurrence of the access event, and the control server transmits the access alert signal to the user client device.

\* \* \* \* \*